United States Patent [19]
Warne et al.

[11] Patent Number: 6,126,933
[45] Date of Patent: Oct. 3, 2000

[54] METHODS OF TREATING INFLAMMATORY BOWEL DISEASES BY ADMINISTERING IL-11

[75] Inventors: Nick W. Warne, Andover; Camille L. Bedrosian, Belmont Hills; James C. Keith, Jr., Andover; Ullrich S. Schwertschlag, Beverly Farms; Paul F. Schendel, Wayland, all of Mass.

[73] Assignee: Genetics Institute, Cambridge, Mass.

[21] Appl. No.: 09/179,026

[22] Filed: Oct. 26, 1998

Related U.S. Application Data

[60] Continuation-in-part of application No. 08/892,407, Jul. 15, 1997, Pat. No. 5,948,402, which is a division of application No. 08/495,724, Jun. 27, 1995, Pat. No. 5,679,339.

[30] Foreign Application Priority Data

May 30, 1996 [WO] WIPO ................... PCT/US96/08059

[51] Int. Cl.⁷ ................................................... A61K 38/19
[52] U.S. Cl. ........................... 424/85.2; 424/85.1; 514/2; 514/8; 514/12; 514/885; 514/867
[58] Field of Search .................... 514/2, 8, 12, 885; 514/867; 424/85.1, 85.2

[56] References Cited

U.S. PATENT DOCUMENTS

| | | | |
|---|---|---|---|
| 4,496,537 | 1/1985 | Kwan | 424/85 |
| 4,675,183 | 6/1987 | Kato et al. | 424/85 |
| 5,215,743 | 6/1993 | Singh et al. | 424/85.1 |
| 5,215,895 | 6/1993 | Bennett et al. | 435/69.52 |
| 5,236,704 | 8/1993 | Fujioka | 424/85.1 |
| 5,270,181 | 12/1993 | McCoy et al. | 435/69.7 |
| 5,292,646 | 3/1994 | McCoy et al. | 435/69.7 |
| 5,358,708 | 10/1994 | Patel | 435/69.52 |
| 5,371,193 | 12/1994 | Bennett et al. | 530/351 |
| 5,700,664 | 12/1997 | Yang et al. | 435/69.52 |

FOREIGN PATENT DOCUMENTS

| | | |
|---|---|---|
| 0 158 487 A2 | 10/1985 | European Pat. Off. . |
| 0 578 823 A1 | 1/1994 | European Pat. Off. . |
| WO 91/07495 A1 | 5/1991 | WIPO . |
| WO 94/05318 A1 | 3/1994 | WIPO . |
| WO 95/24650 A2 | 9/1995 | WIPO . |

OTHER PUBLICATIONS

Manning, et al., Pharmaceutical Research 6:903–918 (1989).
Hamblin, "Cytokines and Cytokine Receptors," IRL Press, pp. 10, 15, 34, 1993.
Paul et al., PNAS, vol. 87, pp. 7512–7516, 1990.
Cherel et al., Blood, vol. 86(7), pp. 2534–2540, 1995.
Kopf et al., Nature, vol. 36(6464), pp. 339–342, 1994.
Neben et al., Stem Cells (Dayt), vol. 11, Supp. 2, pp. 156–162, Jul. 1993.
Sinkae et al., Jons. Interferon Res., vol. 13 (Suppl. 1), p. S77, 1993.
Pikal, BioPharm, vol. 3, No. 9, pp. 26–30, Oct. 1990.
V. P. Zav'yalov et al., "Theoretical conformational analysis of a family of α–helical immunocytokines", Biochimica et Biophisica Acta, 1041, pp. 178–185, 1990.
P. Manavalan et al., "Sequence and Structural Relationships in the Cytokine Family", Journal of Protein Chemistry, vol. 11, No. 3, 1992.
A. G. Bruce et al., "ONCOSTATIN M", Progress in Growth Factor Research, vol. 4, pp. 157–170, 1992.
E. Minasian et al., "A review of cytokine structure", Protein Seq. Data Anal., vol. 5, pp. 57–64, 1992.
W. Strober et al., "The Interleukins", Pediatric Research, vol. 24, No. 5, pp. 549–557, 1988.
J.P. Leonard et al., *J.Exp.Med* 181:381–386 (1995).
R.H. Scofield et al., *PNAS* 90:9330–9334 (1993).
R.E. Hammer et al., *Cell* 63:1099–1112 (1990).
Sonis, et al., Proceedings of the American Assoc. for Cancer Research 36:368 (1995) (abstract 2190).
Keith, Jr. et al., Gastroenterology 108(4):A846 (1995) (abstract).
Keith, Jr. et al., Gastroenterology 106(4):A708 (1994) (abstract).
Keith, Jr. et al., Stem Cells 12(S1):79–90 (1994).
Opal, et al., Blood 86(10):498A (1995) (abstract).
Sonis, et al., European Journal of Cancer, Part B, Oral Oncology 31B(4):261–266 (1995).
M. Feldmann et al., "Role of Cytokines in Rheumatoid Arthritis", Annu. Rev. Immunol., vol. 14, pp. 397–440, 1996.
G. Girasole et al., "Interleukin–11, A New Cytokine Critical for Osteoclast Development", The Journal of Clinical Investigation, Inc., vol. 93, pp. 1515–1524, 1994.
W. E. Paul in: "Fundamental Immunology", Editor, W. E. Paul, Publisher, Raven Press, 1996, New York.
F. M. Brennan, "Role of cytokines in experimental arthritis", Clin. Exp. Immunol., 97:1–13, 1994.
Wang et al., "Parenteral Formulations of Proteins and Peptides: Stability and Stabilizers", J. Of Parenteral Sci and Tech, vol. 6(1), pp. 902–918, 1989.

*Primary Examiner*—Prema Mertz
*Attorney, Agent, or Firm*—Luann Cserr; Barbara Gyure

[57] ABSTRACT

Provided by the present invention are topical formulations of Interleukin-11 and methods for treating a variety of disorders, including inflammatory bowel diseases (e.g., Crohn's disease, ulcerative colitis, indeterminate colitis, and infectious colitis), mucositis (e.g., oral mucositis, gastrointestinal mucositis, nasal mucositis, and proctitis), necrotizing enterocolitis, inflammatory skin disorders (e.g., psoriasis, atopic dermatitis, and contact hypersensitivity), aphthous ulcers, pharyngitis, esophagitis, peptic ulcers, gingivitis, periodontitis, and ocular diseases (e.g., conjunctivitis, retinitis, and uveitis).

19 Claims, No Drawings

METHODS OF TREATING INFLAMMATORY BOWEL DISEASES BY ADMINISTERING IL-11

CROSS-REFERENCE TO RELATED APPLICATIONS

This is a continuation-in-part of U.S. patent application Ser. No. 08/892,407, filed Jul. 15, 1997 now U.S. Pat. No. 5,948,402 which is a divisional of U.S. patent application Ser. No. 08/495,724, filed Jun. 27, 1995, now U.S. Pat. No. 5,679,339, issued Oct. 21, 1997.

FIELD OF INVENTION

The present invention relates generally to novel compositions and methods for topical delivery of interleukin-11 (IL-11). In preferred embodiments, patients are treated employing topical delivery of recombinant human IL-11 for inflammatory bowel diseases (e.g., Crohn's disease, ulcerative colitis, indeterminate colitis, and infectious colitis), mucositis (e.g., oral mucositis, gastrointestinal mucositis, nasal mucositis, and proctitis), necrotizing enterocolitis, inflammatory skin disorders (e.g., psoriasis, atopic dermatitis, and contact hypersensitivity), aphthous ulcers, pharyngitis, esophagitis, peptic ulcers, gingivitis, periodontitis, and ocular diseases (e.g., conjunctivitis, retinitis, and uveitis).

BACKGROUND OF THE INVENTION

Inflammatory responses include a broad range of host reaction to a variety of insults, such as injury, infection, or rejection. It is the overproduction of mediators that is believed to be associated with a broad range of disorders, including AIDS, arthritis (rheumatoid arthritis, osteoarthritis, spondyloarthropathies), antibiotic-induced diarrheal diseases, multiple sclerosis, osteoporosis, gingivitis, peptic ulcer disease, esophagitis, diabetes, retinitis, uveitis, reperfusion injury after myocardial infarction, cerebral vascular accident, aphthous ulcers (oral), atherosclerosis, tumor metastases, asthma, preeclarnpsia, pancreatitis, psoriasis, infertility and allergic disorders such as rhinitis, conjunctivitis, and urticaria.

Some of these disorders and their symptoms are briefly summarized below. According to the methods of the present invention, IL-11 is administered topically to modulate the host's over reaction at the site of insult, thereby treating the following disorders.

Inflammatory Bowel Disease:

Inflammatory bowel disease is the term generally applied to four diseases of the bowel, namely Crohn's disease, ulcerative colitis, indeterminate colitis, and infectious colitis.

Ulcerative Colitis:

Ulcerative colitis is a chronic inflammatory disease of unknown etiology afflicting the large intestine. The course of the disease may be continuous or relapsing, mild or severe. The earliest lesion is an inflammatory infiltration with abscess formation at the base of the crypts of Lieberkühn. Coalescence of these distended and ruptured crypts tends to separate the overlying mucosa from its blood supply, leading to ulceration. Signs and symptoms of the disease include cramping, lower abdominal pain, rectal bleeding, and frequent, loose discharges consisting mainly of blood, pus, and mucus with scanty fecal particles. A total colectomy may be required for acute severe or chronic, unremitting ulcerative colitis.

Crohn's Disease:

Crohn's disease (also known as regional enteritis or ulcerative ileitis) is also a chronic inflammatory disease of unknown etiology but, unlike ulcerative colitis, it can affect any part of the bowel. The most prominent feature of the disease is the granular, reddish-purple edematous thickening of the bowel wall. With the development of inflammation, these granulomas often lose their circumscribed borders and integrate with the surrounding tissue. Diarrhea and obstruction of the bowel are the predominant clinical features. As with ulcerative colitis, the course of the disease may be continuous or relapsing, mild or severe but, unlike ulcerative colitis, it is not curable by resection of the involved segment of bowel. Most patients with Crohn's disease require surgery at some point, but subsequent relapse is common and continuous medical treatment is usual.

Mucositis:

Mucositis involves ulcerative breakdown of mucosal epithelial tissue, and is literally defined as inflammation of the mucous membrane. The pathophysiology of mucositis in response to toxic insults to the mucosa by chemotherapy or by ionizing radiation is complex and involves a cascade of interactions among cells, cytokines and the oral microflora. The underlying premise for susceptibility of the mucosa of the oropharynx and gastrointestinal tract to chemotherapy or radiation damage is related to rapid epithelial stem cell turnover. Mucositis may be characterized by the following phases:

1. Early inflammatory phase characterized by release of inflammatory cytokines in response to local tissue damage caused by cytotoxic agent(s);
2. Epithelial phase characterized by death of basal cells, which hinders repopulation of the epithelium. This inability to regenerate leads to atrophy followed by ulceration. The ulceration represents loss of an important anatomic barrier at a site of local microflora;
3. Infection phase characterized by local invasion of microflora that results in an inflammatory response to the local infection. The inflammation results in additional local tissue damage and possibly erosive ulceration; and
4. Healing phase characterized by resolution of the infection and regeneration of epithelium.

Oral mucositis produces the following clinical symptoms and signs resulting from cellular damage: 1) sensation of dryness; 2) asymptomatic redness and erythema; 3) solitary white elevated desquamative patches which are painful upon pressure contact; and 4) large, painful, contiguous pseudomembranous lesions associated with dysphagia and decreased oral intake. These spontaneously painful lesions histopathologically show loss of epithelial cells to the basement membrane, which exposes the connective tissue stroma with its associated innervation.

As with oral mucosa, gastrointestinal mucosal damage results from disturbance of cellular mitosis that leads to reduction in the turnover rate of the basal cells of the intestinal crypts. The symptoms and signs of gastrointestinal mucositis include tenesmus (painful ineffectual straining at stool), pain, bleeding, diarrhea, telangectasia (neovascularization), and progression to ulceration. Early signs of diarrhea include increased stool frequency, loose or watery stool, food aversion, increased bowel sounds, abdominal pain, and some loss of skin turgor indicative of dehydration. When the diarrhea is severe it may be associated with mucosal ulceration, bleeding, intestinal perforation and proctitis. Stool exam may reveal occult blood and fecal leukocytes.

Necrotizing Enterocolitis:

Necrotizing enterocolits is an inflammatory disease of unknown etiology that afflicts between 1–5% of all infants admitted to neonatal intensive care units, most of whom are premature infants. Signs and symptoms include abdominal distention, gastrointestinal hemorrhage, and feeding intolerance. The disease most often involves the ileum and colon, and is characterized by loss of epithelium and submucosal edema, ulcerations, and, in severe cases, transmural necrosis.

Psoriasis:

Psoriasis is a chronic inflammatory skin disorder involving hyperproliferation of the epidermis and inflammation of both the epidermis and the dermis. Macrophage, T-cells and neutrophil infiltration of the dermis and epidermis is seen, and proinflammatory mediators are released from these activated cells.

Aphthous Ulcers (oral):

Although the cause of aphthous ulcers remain unknown, many physicians believe they are caused by autoimmune phenomena, which cause the destruction of discrete areas of the oral mucosa which leads to oral ulceration. Among the cytokines present in these active areas of ulceration, TNF-$\alpha$ appears to play a predominant role.

Gingivitis:

Adult periodontitis is strongly associated with infection by *Porphyromonas gingivalis*. Proteolytic enzymes, which are produced in large quantity by this bacteria, are considered as important pathogenic agents. The increased production and flow of gingival crevicular fluid (GCF) is an important change in gingival tissues during periodontal infection, correlating with clinical indices of gingival inflammation. Indeed, salivary protein and albumin concentrations of individuals with periodontitis, which are an indication of plasma leakage due to vascular permeability enhancement (VPE), are significantly increased compared to healthy subjects. The production of GCF appears dependent on VPE induced at periodontitis sites, presumably involving proteinase(s) of *P. gingivalis* in their generation.

Esophagitis:

The most common cause of esophagitis is the chronic reflux of hydrochloric acid from the stomach due to inefficiency of the cardiac sphincter of the stomach. The chronic presence of acid in the lower esophagus leads to damage of the esophageal mucosa. In the most severe form, a syndrome called Barrett's esophagus can develop which often leads to esophageal cancer. Other causes of esophagitis include parenteral chemotherapy and ionizing radiation, associated with radiation therapy for cancer in the thoracic cavity.

Retinitis:

Inflammation of the light sensitive retina, retinitis, can occur due to a variety of viral, bacterial or autoimmune etiologies. The end result is destruction of the retina and loss of sight.

Uveitis:

Inflammation of the anterior portion of the eye its associated structures, the iris and cornea occurs with a relatively high frequency in patients with autoimmune disorders.

Peptic Ulcer Disease:

Inhibition of gastric acid secretion with $H_2$-receptor antagonists and, more recently, blockers of $H^+,K^+$-ATPase (also known as the proton pump) has been the mainstay of therapy for peptic ulcer disease. The pathophysiology of peptic ulcers remains obscure. An appreciation of the complexity of the physiology of the gastric mucosa has led to a hypothesis that peptic ulcers are the result of an imbalance in the relative importance of aggressive (acid, pepsin) and protective (mucus, bicarbonate, blood flow, prostaglandins, etc.) factors. Infection of the mucosa of the human gastric antrum with the bacterium *Helicobacter pylori* has been widely accepted as the cause of chronic, active, type B gastritis. Further, this form of gastritis has been linked directly to peptic ulcer disease by studies showing that eradication of *H. pylon* reverses this gastritis and prevents duodenal ulcer relapse. Because cytokines are the principal mediators by which immune/inflammatory cells communicate with each other and with other cells, it is likely that these small peptides are involved in the pathogenesis of chronic active type B gastritis and the resulting peptic ulcer disease.

Some cytokines (IL-1, epidermal growth factor, transforming growth factor-$\alpha$, acidic and basic fibroblast growth factors) tip the balance towards peptic ulcer healing; others (tumor necrosis factor-$\alpha$) appear to have no effect; still others (IL-4) may even cause gastrointestinal damage.

The infiltration and activation of multiple types of inflammatory cells result in a series of degenerative changes in the vasculature of the affected area, as well as inciting damage of the surrounding parenchymal tissue.

BRIEF SUMMARY OF THE INVENTION

Provided by the present invention are novel compositions for the topical administration of IL-11 in order to treat a number of disorders where such administration is preferable to systemic administration. Among the reasons that local administration may be preferred are the ease of administering a topical formulation compared to administration of subcutaneous injectable formulations. In certain classes of patients, the toxicity profile of chemotherapeutic agents may be such that concurrent parenteral administration of IL-11 is relatively unsuited. Other patients may have medical conditions for which the adverse event profile of parenteral IL-11 is relatively unsuited.

According to the present invention, IL-11, analogs, and derivatives thereof, are administered to patients, either prophylactically or at the onset of symptoms associated with the aforementioned disorders, through one of several forms of local administration described below. IL-11 can be administered in suitable pharmaceutically acceptable carriers either alone or in combination with other conventional agents useful in alleviating the symptoms associated with the aforementioned disorders.

In one embodiment, the present invention comprises preparations of IL-11 which are suitable for oral delivery to the mouth. Suitable oral preparations may be prepared with aqueous-based solutions such as sodium bicarbonate (e.g., Brioschi®), or in gels and suspensions for topical administration in the mouth. Oral preparations may also take the form of patches for delivery of IL-11 to the mouth via sustained release. Additional oral preparations may comprise IL-11 in the form of a lozenge or an uncoated tablet which is retained in the mouth. The oral preparations are particularly well-suited for disorders and inflammatory responses involving the mucosa of the head, neck and/or mouth. Such conditions include oral mucositis, pharyngitis, esophagitis, gingivitis, periodontitis, and aphthous ulcers (oral). Such conditions may result, for example, from chemotherapy or radiotherapy for head and neck cancer, cervical esophageal cancer or lung cancer.

In other embodiments, the present invention comprises preparations of IL-11 which are suitable for topical delivery for mucosa and/or dermis. Such topical preparations may be prepared in the form of aqueous-based solutions, gels, ointments or creams for topical administration, as gels and suspensions for cervical administration, as pills, tablets, capsules or suppositories for immediate or sustained release to the gastrointestinal tract, or in the form of solution for enema. Such topical preparations are especially suited for treatment of disorders relating to local regions, such as psoriasis, as well as inflammatory bowel disease, esophagitis, and gastrointestinal mucositis. Some of these conditions may result, for example, from chemotherapy and/or radiotherapy for colorectal cancer, prostate cancer, cervical esophageal cancer or lung cancer.

Suitable doses of IL-11 are generally in the range of between about 1 and about 250 µg/kg body weight, and may be administered from once a week up to about six times daily. Treatment may continue for a period of between one day and six months, or for as long as is deemed necessary and safe in the treatment of the aforementioned disorders, as is readily ascertained by standard tests by the attending physician, depending upon the nature of the disorder being treated.

DETAILED DESCRIPTION OF THE INVENTION

Provided by the present invention are methods and compositions for topical administration of IL-11, for the treatment of various disorders, such as inflammatory bowel diseases (e.g., Crohn's disease, ulcerative colitis, indeterminate colitis, and infectious colitis), mucositis (e.g., oral mucositis, gastrointestinal mucositis, nasal mucositis, and proctitis), necrotizing enterocolitis, aphthous ulcers, psoriasis, pharyngitis, esophagitis, peptic ulcers, gingivitis, periodontitis, and ocular diseases (e.g., conjunctivitis, retinitis, and uveitis).

Unless defined otherwise, all technical and scientific terms used herein have the same meaning as commonly understood by one of ordinary skill in the art to which this invention pertains. Although any methods and materials similar or equivalent to those described herein can be used in the practice of the present invention, the preferred methods and materials are described. For purposes of the present invention, the following terms are defined below.

As used herein, the term "topical" refers to application at the site of inflammation (i.e., non-systemic administration), and includes, for example, oral, intranasal, intrabronchial, topical, and rectal routes of administration. The term "topical formulation" refers to a pharmaceutical formulation which is suitable for topical administration of the active ingredient.

As used herein, the term "pharmaceutically acceptable" refers to a carrier medium which does not interfere with the effectiveness of the biological activity of the active ingredient(s) and which is not toxic to the host to which it is administered.

As used herein, the terms "therapeutically effective amount" and "therapeutically effective dose" as applied to the active ingredient refers to the amount of the component in the composition or administered to the host that results in an increase in the therapeutic index of the host. The "therapeutic index" can be defined for purposes herein in terms of efficacy, i.e., extent of reduction or inhibition of inflammation. Suitable doses of the active ingredient can be determined using well-known methods, a variety of which are known and readily available in the pharmaceutical sciences, including, for example, measurement of markers associated with the disorder (e.g., TNF-α, IL-1β, IL-6, and/or IL-12 p40 mRNA), the biological effects of TNF-α, and decreased symptomatology.

Interleukin 11 (IL-11) is a pleiotropic cytokine that stimulates primitive lymphohematopoietic progenitor cells and synergizes with other hematopoietic growth factors to stimulate the proliferation and maturation of megakaryocytes. IL-11 is described in detail in International Application PCTIUS90/06803, published May 30, 1991, as well as in U.S. Pat. No. 5,215,895; issued June 1, 1993. A cloned human IL-11 was previously deposited with the ATCC, 10801 University Boulevard, Manassas, Va. 20110-2209, on Mar. 30, 1990 under ATCC No. 68284. Moreover, as described in U.S. Pat. No. 5,270,181, issued Dec. 14, 1993, and U.S. Pat. No. 5,292,646, issued Mar. 8, 1994, IL-11 may also be produced recombinantly as a fusion protein with another protein. IL-11 can be produced in a variety of host cells by resort to now conventional genetic engineering techniques. In addition, IL-11 can be obtained from various cell lines, for example, the human lung fibroblast cell line, MRC-5 (ATCC Accession No. CCL 171), and Paul et al., the human trophoblastic cell line, TPA30-1 (ATCC Accession No. CRL 1583). A cDNA encoding human IL-11, as well as the deduced amino acid sequence (amino acids 1 to 199), is described in Proc. Natl. Acad. Sci. USA 87:7512 (1990). U.S. Pat. No. 5,292,646, supra, describes a des-Pro form of IL-11 in which the N-terminal proline of the mature form of IL-11 (amino acids 22–199) has been removed (amino acids 23–199). As is appreciated by one skilled in the art, any form of IL-11 which retains IL-11 activity, such as variants through the substitution or deletion of amino acids, analogs and derivatives of IL-11, is useful according to the present invention. The disclosure of each of the above publications is hereby incorporated by reference for the contents thereof.

In addition to recombinant techniques, IL-11 may also be produced by known conventional chemical synthesis. Methods for constructing the polypeptides useful in the present invention by synthetic means are known to those of skill in the art. The synthetically constructed cytokine polypeptide sequences, by virtue of sharing primary, secondary, or tertiary structural and conformational characteristics with the natural cytokine polypeptides are anticipated to possess biological activities in common therewith. Such synthetically constructed cytokine polypeptide sequences or fragments thereof, which duplicate or partially duplicate the functionality thereof may also be used in the method of this invention. Thus, they may be employed as biologically active or immunological substitutes for the natural, purified cytokines useful in the present invention.

Modifications in the protein, peptide or DNA sequences of these cytokines or active fragments thereof may also produce proteins which may be employed in the methods of this invention. Such modified cytokines can be made by one skilled in the art using known techniques. Modifications of interest in the cytokine sequences, e.g., the IL-11 sequence, may include the replacement, insertion or deletion of one or more selected amino acid residues in the coding sequences. Mutagenic techniques for such replacement, insertion or deletion are well known to one skilled in the art. (See, e.g., U.S. Pat. No. 4,518,584.)

Other specific mutations of the sequences of the cytokine polypeptides which may be useful therapeutically as described herein may involve, e.g., the insertion of one or more glycosylation sites. An asparagine-linked glycosylation recognition site can be inserted into the sequence by the deletion, substitution or addition of amino acids into the peptide sequence or nucleotides into the DNA sequence. Such changes may be made at any site of the molecule that is modified by addition of O-linked carbohydrate. Expression of such altered nucleotide or peptide sequences produces variants which may be glycosylated at those sites.

Additional analogs and derivatives of the sequence of the selected cytokine which would be expected to retain or prolong its activity in whole or in part, and which are expected to be useful in the present method, may also be easily made by one of skill in the art. One such modification may be the attachment of polyethylene glycol (PEG) onto existing lysine residues in the cytokine sequence or the insertion of one or more lysine residues or other amino acid residues that can react with PEG or PEG derivatives into the sequence by conventional techniques to enable the attachment of PEG moieties.

Additional analogs of these selected cytokines may also be characterized by allelic variations in the DNA sequences encoding them, or induced variations in the DNA sequences encoding them. It is anticipated that all analogs disclosed in the above-referenced publications, including those characterized by DNA sequences capable of hybridizing to the disclosed cytokine sequences under stringent hybridization conditions or non-stringent conditions (Sambrook et al, Molecular Cloning. A Laboratory Manual, 2d edit., Cold Spring Harbor Laboratory, N.Y. (1989)) will be similarly useful in this invention.

Also considered as derivatives useful in these methods are fusion molecules, prepared by fusing the sequence or a biologically active fragment of the sequence of one cytokine to another cytokine or proteinaceous therapeutic agent, e.g., IL-11 fused to IL-6 (see, e.g., methods for fusion described in PCT/US91/06186 (WO92/04455), published Mar. 19, 1992). Alternatively, combinations of the cytokines may be administered together according to the method.

Thus, where in the description of the methods of this invention IL-11 is mentioned by name, it is understood by those of skill in the art that IL-11 encompasses the protein produced by the sequences presently disclosed in the art, as well as proteins characterized by the modifications described above yet which retain substantially similar activity. Standard laboratory tests are utilized to monitor progress of the treatment. Levels of TNF-α in serum or the biologic effects of TNF-α could be followed in a variety of these diseases. Decreased symptomatology could also be used to monitor the effectiveness of treatment as is well known to physicians skilled in the art of treating such disorders. Treatment is preferably prophylactic, but may also be at the onset of symptoms associated with the aforementioned disorders.

In one aspect of the invention, IL-11 is used in a therapeutic composition to alleviate or prevent the onset of symptoms associated with an inflammatory disorder. While it is possible to administer IL-11 alone, it is believed preferable to present it as part of a pharmaceutical formulation. In accordance with this aspect of the invention, the pharmaceutical compositions comprise IL-11 in a therapeutically effective dose together with one or more pharmaceutically acceptable carriers and optionally other therapeutic ingredients. A wide variety of pharmaceutically acceptable carriers are known to those of skill in the art. See, e.g., Remington's Pharmaceutical Sciences, Mack Publishing Co., Easton, Pa, 17th ed. (1985), which is incorporated by reference herein. Preferred carriers include inert, non-toxic solids (e.g., dextrose, dextrin, cellulose, pectin, starch, lactose, sucrose, and calcium phosphate,), semi-solids (e.g., glycerol stearate, polyethylene glycol, stearic acid, agar, gelatin, and propylene glycol) and liquids (e.g., buffered saline, water, an organic solvent, and pharmaceutically acceptable oils or fats).

As will be appreciated by those of skill in the art, the preferred form of the pharmaceutical composition of IL-11 will depend on the intended mode of administration, which in turn will depend on the location and nature of the inflammatory disorder to be treated. For example, delivery to the mouth (e.g., for treatment of oral mucositis, aphthous ulcers, gingivitis, periodontitis), head and/or neck (e.g., for treatment of pharyngitis, esophagitis) can be in the form of aqueous-based oral solutions, suspensions, emulsions, syrups, elixirs, gels, patches, lozenges, tablets, or capsules. Delivery to the gastrointestinal tract (e.g., for treatment of gastrointestinal mucositis, peptic ulcers and inflammatory bowel diseases, such as Crohn's disease, ulcerative colitis, indeterminate colitis, and infectious colitis) can be in the form of oral solutions, gels, suspensions, tablets, capsules, and the like. IL-11, either alone or in combination with other components in a pharmaceutical composition, can be added to infant formula for delivery to the gastrointestinal tract of an infant suffering from or susceptible to necrotizing enterocolitis. It is also possible to formulate the IL-11 preparation for rectal administration (e.g., for treatment of proctitis), e.g., in the form of enema, suppositories, rectal-foam, and the like. Delivery to the eye (e.g., for treatment of ocular diseases such as conjunctivitis, retinitis, and uveitis) can be in the form of solutions, gels, or suspensions. Delivery to the nose (e.g., for treatment of nasal mucositis) can be in the form of solutions, gels, or suspensions. The intranasal formulations may be formulated, for example, into an aqueous or partially aqueous solution, which can then be utilized in the form of a nasal drop or an aerosol. Delivery to the skin (e.g., for treatment of psoriasis) can be in the form of aqueous-based solutions, gels, suspensions, lotions, creams, ointments, patches, and the like.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral administration include water (partially containing additives as above), alcohols (including monohydric alcohols and polyhydric alcohols, e.g., glycols) and their derivatives, oils (e.g., peanut oil, sesame oil, olive oil, and coconut oil), and combinations of the above. Compositions comprising such carriers and adjuvants may be formulated using well known conventional materials and methods. Such materials and methods are described, for example, in Remington's Pharmaceutical Sciences, supra. Infant formula is also a suitable liquid carrier, particularly when the pharmaceutical composition is used to treat or prevent necrotizing enterocolitis.

A solid carrier can include one or more substances which may also act as flavoring agents, lubricants, solubilizers, suspending agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablet preferably contain up to 99% of the active ingredient, and may be formulated for immediate and/or sustained release of the active ingredient. Suitable solid carriers include, for example, calcium or sodium phosphate, magnesium stearate, talc, sugars, glycine, lactose, dextrin, starch, gelatin, cellulose, cellulose derivatives (e.g., methyl cellulose, hydroxypropylmethyl cellulose, and sodium carboxymethyl cellulose), polyvinylpyrrolidone, low melting point waxes, and combinations of the above.

Oral tablets may be prepared using a variety of well known methods and in a variety of conventional forms. Exemplary forms include dry powder compaction tablets, micro-particulate systems (e.g., wherein the active ingredient is spray-dried onto a scaffold particle), and hard or soft-gel capsules. The tablets may be optionally covered with an enteric coating, which remains intact in the stomach, but will dissolve and release the contents of the tablet once it reaches the small intestine. Most currently used enteric coatings are those which remain undissociated in the low pH environment of the stomach, but readily solubilize when the pH rises to about 4 or 5. A number of commercially available enteric coatings may be used depending on the target part of the intestinal tract, i.e., the site of the inflammatory bowel disorder in the patient. Such coatings include, for example, methacrylic acid-methacrylic acid ester-based copolymer, which is sold under the trade name "Eudragit"; anionic water-soluble, polymer cellulose ether, which is sold under the trade name "Aqualon"; cellulose acetate phthalate; polyvinyl acetate phthalate; hydroxypropyl methylcellulose phthalate; and the like. Compositions comprising such carriers and adjuvants may be formulated, and tablets prepared from such compositions, using well known conventional materials and methods. Such materials and methods are described, for example, in *Remington's Pharmaceutical Sciences*, supra.

In one embodiment of the invention, the pharmaceutical composition comprises one or more sustained or controlled release excipients such that a slow or sustained, preferably constant, release of the active ingredient is achieved. A wide variety of suitable excipients are known in the art and are not a part of this invention. Such sustained/controlled release excipients and systems are described, for example, in U.S. Pat. No. 5,612,053 (Baichwal et al.), U.S. Pat. No. 5,554,387 (Baichwal), U.S. Pat. No. 5,512,297 (Baichwal), U.S. Pat. No. 5,478,574 (Baichwal et al.), and U.S. Pat. No. 5,472,711 (Baichwal et al.), each of which is incorporated by reference herein. If desired, the pharmaceutical composition can be formulated to provide a pulse dose of the active ingredient. A variety of pulse-dose systems, which provide low or high-pulsed doses, are known in the art and are not a part of this invention. Such pulse-dose formulations are described, for example, in Y.H. Bae, "Stimuli-Sensitive Drug Delivery," *Controlled Drug Delivery* (ed. K. Park) ACS Press, Washington, D.C. (1997); *Drugs* (1982) 23:207–226; *Fertl.Steril.* (1983) 39:695–699, 1983; *Brit. J. Cancer* (1982) 45:86–94; *Int. J. Radiat. OncoL BioL Phys.* (1982) 8:915–919; *J. Clin. EndocrinoL Metab.* (1981) 53:184–91; and *Diabetes* (1977) 26:571–581.

In another embodiment of the invention, the pharmaceutical composition is formulated to provide direct and/or targeted delivery of the active ingredient to a specific anatomic site or sites within the gastrointestinal tract; e.g., the duodenum, jejunum, ileum, cecum and/or colon, each of which is believed to contain receptors for IL-11. Methods for providing targeted delivery of macromolecules, including proteins and polypeptides, to specific tissues or organs within a mammalian host are well known in the art and not a part of this invention. Such targeted delivery systems are described, for example, in R. J. Mrsny, "Site-Specific Drug Delivery in the Gastrointestinal Tract," *Controlled Drug Delivery*, supra; M. Mezei and D. Meisner, "Liposomes and Nanoparticles as Ocular Drug Delivery Systems," *Biopharmaceutics of Ocular Drug Delivery*, Ch. 6 (ed. P. Edman) CRC Press, Boca Raton, Fla. (1992); T. L. Bowersock and H. Hogenesch, "Oral Immunization Using Microparticles," *Controlled Drug Delivery*, supra; M. Mezei, "Liposomes in Topical Application of Drugs," *Liposomes as Drug Carriers: Trends and Progress* (ed. G. Gregoriadis), J. Wiley & Sons Publ. USA (1988), pp. 663–677; and J. J. Berti and J. J. Lipsky, "Transcutaneous Drug Delivery: A Practical Review," *Mayo CLW Proc.* (1995) 70:581–586.

IL-11, either alone or in combination with other therapeutic agents, may also be administered topically in the form of a dermal patch or transdermal delivery system. Such patches and systems are especially suited for treatment of inflammatory skin disorders such as psoriasis, and for inflammatory disorders involving the mucosa of the head, neck and/or mouth, e.g., oral mucositis, pharyngitis, esophagitis, gingivitis, perodontitis, and aphthous ulcers. In this embodiment of the invention, the pharmaceutical composition may be administered through the use of a dermal patch containing the active ingredient(s) and a carrier that is inert to the active ingredient(s), non-toxic to the skin or mucosal epithelium, and allows delivery of the agent to the dermis and/or epithelium. Dermal patches and delivery systems, utilizing active or passive transdermal delivery carriers, comprising IL-11 may be prepared suing well known methods and materials, including, for example, microporous membranes, silicon polymers and diffusion matrixes. Such materials and methods are described, for example, in *Remington's Pharmaceutical Sciences*, supra.

In yet another embodiment of the invention, at least one proteinase inhibitor is combined with IL-11 in a therapeutic composition to treat inflammatory diseases. In accordance with this aspect of the invention, the pharmaceutical composition comprises IL-11 and one or more proteinase inhibitors, which stabilize the IL-11 molecule against proteolytic degradation. It may be preferable to include a proteinase inhibitor in the pharmaceutical composition to protect IL-11 against proteolytic enzymes in the gastrointestinal tract, particularly in rectal formulations. A wide variety of suitable proteinase inhibitors are known in the art and are not a part of this invention. Suitable proteinase inhibitors include, for example, aprotinin, a kallikrein-trypsin inhibitor, and protein serine proteinase inhibitors such as α-macroglobulin, soybean trypsin inhibitor, and ovomucoid.

A suitable treatment regimen for patients undergoing treatment, including for example prophylactic treatment, may be determined by the attending physician based upon such factors as the patient's age, sex, weight, and general health. Generally, a suitable dose of IL-11 ranges broadly, preferably between about 1 and about 250 microgram ($\mu$g) per kilogram (kg) of body weight of recipient per treatment. Another suitable dose may be in the range of about 1 to about 100 $\mu$g per kg of body weight, and more preferably in the range of about 10 to about 50 $\mu$g per kg of body weight. If desired, these doses can be adjusted to units. A unit is conventionally described as the concentration of polypeptide which leads to half-maximal stimulation in a suitable assay, e.g., for IL-11, the T1165 assay described in PCT/US90/06803. Doses may be administered daily for between one day and six months, or for as long as is deemed necessary and safe, as is readily ascertained by standard tests by the attending physician, depending upon the nature of the disorder being treated. Where appropriate, the dosages may be adjusted upward or downward, for example, a dosing regimen requiring administration of IL-11 at a dose of 25 $\mu$g/kg, daily for one week, or fewer days, or multiple weeks if indicated. The progress of treatment is appropriately monitored by measurement of markers associated with the disorder being treated to determine if such a dose results in a decrease of for example, TNF-α levels (or corresponding marker) and if not, increasing the dose two-fold for an additional time period of treatment and measurement of marker levels until an effective dosing regimen is reached.

The following examples illustrate the methods of the present invention and in particular the use of topical IL-11 formulations in treating Crohn's disease, chemotherapy-induced ulcerative mucositis, colitis (colonic ulcers), psoriasis, and inflammatory bowel disease. However, as the skilled artisan will recognize from the present disclosure, numerous modifications and variations are possible and comprised within the present invention. The examples are not exhaustive, and do not limit the scope of the invention in any way.

EXAMPLE 1

TREATMENT OF INFLAMMATORY BOWEL DISEASE

In two well-established models it has been shown that subcutaneous rhIL-11 is able to significantly reduce the clinical signs and histologic lesions of gastrointestinal inflammation: acetic acid-induced colitis, a model of acute injury; and the HLA-B27 transgenic rat, a model of chronic inflammation. While conducting further studies of the mechanism of rhIL-11 action, oral topical activity was seen in hamsters with 5-FU induced oral mucositis and mucosal activity was documented in in vitro/ ex vivo studies of intestinal transport. Subsequently, these models have been used to confirm the effectiveness of topically and orally administered rhIL-11.

Applicants first examined local topical delivery of rhIL-11 to the colon by enema. To determine the stability of rhIL-11 in the lumen of the gut, rhIL-11 and intestinal chyme from HLA-B27 rats were combined and incubated at 37° C. for up to several hours in the presence or absence of a proteinase inhibitors. Fluid samples were analyzed periodically by SDS-PAGE. The addition of a proteinase inhibitor, avian ovoinhibitor, stabilized rhIL-11 against the proteolytic degradation observed in the rat chyme. Next, twenty-three HLA-B27 rats (22–23 weeks old) were randomized to one of six treatment groups: rhIL-11 Vehicle; 50 $\mu$g/ml ovoinhibitor; rhIL-11 200 $\mu$g/ml; or rhIL-11 at 50, 200 or 800 $\mu$g/ml combined with 50 $\mu$g/ml of ovoinhibitor. Animals received a colonic irrigation (1ml) of the respective formulations, Monday, Wednesday and Friday, for three weeks. Stool character was assessed daily. At the end of the experiment, terminal blood samples were obtained, and then the animals were euthanized by an overdose of anesthetic. Platelet counts and colonic mucosal lesions were quantitated and analyzed as described previously. Platelet counts were not different in any of the groups. In the vehicle treated animals, normal, soft or diarrhea stools were present at 16.5, 33, or 50% of the total animal observation days, respectively. In the 50 $\mu$g/ml+50 $\mu$g/ml ovoinhibitor animals, normal, soft, or diarrhea stools were present at 65.9, 25, or 9.1% of the total animal observation days, respectively. Histologic lesion scores were 7.25+1.4 and 7.8±1.4 in the vehicle and ovoinhibitor groups, respectively. ANOVA testing showed that all of the rhIL-11 lesion scores were lower than either vehicle or ovoinhibitor (P<0.05) and the lowest lesion score was in the 50 $\mu$g rhIL-11+50 $\mu$g ovoinhibitor group, 2.1±0.4. Topically administered rhIL-11 was beneficial in the model of chronic inflammatory bowel disease when combined with a proteinase inhibitor. Since this study was based around a dose of 200 $\mu$g/ml, no dosing group of 50 $\mu$g/ml without the proteinase inhibitor was included.

Next, the effects of lower doses of recombinant human interleukin eleven (rhIL-11) with or without Aprotinin (an FDA approved and marketed Proteinase inhibitor) delivered by enema were assessed in the acetic acid model of acute colitis. Colitis was induced in the descending colons of 80 anesthetized Sprague-Dawley rats by intraluminal instillation of 10% acetic acid for 10 seconds on Day 0 of the study. The rats were randomly assigned to the 8 groups according to their different treatments as described below:

TABLE 1

| Group | No. Animals | Dosage | Schedule |
|---|---|---|---|
| 1 Vehicle | 10 | 1 ml. Buffer | 3 days/wk/2 wks. |
| 2 Aprotinin | 10 | 50 $\mu$g/ml | 3 days/wk/2 wks. |
| 3 & 4 rhIL-11 ± Aprotinin | 20 | 10 $\mu$g/$\mu$g/ml | 3 days/wk/2 wks |
| 5 & 6 rhIL-11 ± Aprotinin | 20 | 25 $\mu$g/g/ml | 3 days/wk/2 wks |
| 7 & 8 rhIL-11 ± Aprotinin | 20 | 50 $\mu$g/ml | 3 days/wk/2 wks |

Peripheral hematologic parameters were assessed. On day 15, the animals were euthanized, and colons were removed for determination of lesion scores by gross examination and histologic evaluation. Platelet counts in all groups were in normal range. All animals treated with acetic acid developed diffuse colonic lesions, characterized by ulceration, hemorrhage, edema, depletion of goblet cells, and infiltration of leukocytes. The gross and histologic lesions of all rhIL-11 treated animals were significantly reduced compared with vehicle controls on day 15. Administration of rhIL-11 10 $\mu$g with 50 $\mu$g Aprotinin 3 days/week/for 2 weeks or 50 $\mu$g/ml rhIL-11 3 days/wk/2wks appeared to be most effective in this model of colonic mucosal injury.

EXAMPLE 2

TREATMENT OF ORAL MUCOSITIS 95 male Golden Syrian hamsters were equally divided into five groups. Group 1 [control] received phosphate buffered saline and 0.5% hamster serum (vehicle) topically on days 3–14. Groups 2 and 4 received 50 $\mu$g IL-11 subcutaneously, twice daily, on days 0–14 and 3–14, respectively. Groups 3 and 5 received 100 $\mu$g IL-11 topically, four times daily, on days 3–14 and 0–14, respectively. Ulcerative mucositis was induced by administration of 60 mg/kg body weight of 5-fluorouracil on days 0 and 2. The left buccal pouch was superficially irritated on day 4. Ulcerative mucositis was evaluated blindly starting on day 6 by scoring standardized photographs. The scoring was done on a scale of 0–10, with 10 being the most severe. Animals were weighed daily. Blood was taken from 3 animals per group on days 6, 10 and 14.

For the entire experiment, average mean ulcerative mucositis scores for all groups were significantly [p<0.05] lower than control. [G1=5.0; G2=3.8; G3=4.1; G4=3.3; G5=4.0]. Day 14 survival rates for G1 through G5 were 23%; 69%, 38%, 100% and 46%, respectively. Thus, topical administration of IL-11 was shown to favorably modify the course of chemotherapy-induced ulcerative mucositis relative to control.

The present investigation demonstrates the beneficial effects of a topical formulation of recombinant human IL-11

(rhIL-11) on the induction, course and resolution of chemotherapy-induced mucositis.

Materials and Methods

Male LVG Golden Syrian hamsters (Charles River Laboratories, Wilmington, Mass.), aged 5–6 weeks, were caged in small groups and fed standard hamster chow and water ad libitum. All procedures were conducted in accordance with guidelines set by the Harvard Medical Area Standing Committee on Animals.

Mucositis Induction and Evaluation

All procedures were performed using anesthesia induced by diethyl ether. To induce mucositis, 5-fluorouracil was administered (60 mg/kg) by intraperitoneal injection on days 0 and 4. To mimic the functional trauma, which occurs in humans, the left buccal pouch mucosa was superficially irritated on day 4. Animals were weighed and observed daily through day 14. Mucositis was evaluated on days 6 to 14. To evaluate mucositis, animals were anesthetized and the cheek pouch was everted, immobilized, and photographed using a standard, validated technique. At the conclusion of the study, all film was developed simultaneously. Photographs were numbered, randomized and graded blindly by three independent observers using a 10-point scale in which mild mucositis equaled a score of 1 to 3, moderate 4 to 6, and severe greater than 6. Mild mucositis was defined as mucosal erythema with vasodilation. Mold mucositis was defined as ulceration with pseudomembrane formation, erythema and vasodilation, and severe mucositis consisted of diffuse ulceration with extensive areas of necrosis, pseudomembranes, erythema and vasodilation.

Test Groups and Protocol

Ninety-five animals were prospectively randomized into five equal groups. Each animal was individually numbered using an ear punch technique. The following groups were studied:

| | |
|---|---|
| Group 1 | Vehicle control, topical, four times daily, days 3 to 14 (day 0 = day of first chemotherapy injection). |
| Group 2 | 100 μg IL-11 per day in a divided dose given twice daily, subcutaneously, days 0–14. |
| Group 3 | 400 μg IL-11 per day in a divided dose given four times daily, topically, days 3–14. |
| Group 4 | 100 μg IL-11 per day in a divided dose given twice daily, subcutaneously, days 3–14 |
| Group 5 | 400 μg Il-11 per day in a divided dose given four times daily, topically, days 0–14. |

Animals in the Group 1 were treated with topical application of PBS containing 0.5% hamster serum. Animals in the test groups received rhIL-11 made up in PBS containing 0.5% hamster serum. Animals receiving topical therapy received treatment at 9 a.m., 11:30 a.m., 2 p.m. and 4:30 p.m. Animals receiving injections of IL-11 were treated at 9 a.m. and 4 p.m. Whole blood was obtained on days 6 and 14 to evaluated the number of platelets.

Results

Cumulative mean mucositis scores for group 2 (3.0) and group 4 (2.7) were markedly less than that noted for the control (4.7). Topical application of rhIL-11 was of benefit (group 3=3.3; group 5=3.4), though slightly less efficacious than rhIL-11 delivered by the subcutaneous route. Interestingly, the efficacy of rhIL-11 given by either route was essentially comparable after day 10. Marked rhIL-11 benefit was noted from day 6 through day 14 among animals treated via the subcutaneous route. On days 6, 7, and 8, animals in group 2 (IL-11 from day 0) had slightly less mucositis than did animals in group 4 (IL-11 beginning on day 3). On day 9 this trend was reversed. No difference was seen for the remaining days of the study.

Schedule of rhIL-11 administration had no observed effect on its topical efficacy, with no significant differences observed between scores of animals in groups 3 and 5. Less mucositis was observed in animals treated with topically applied rhIL-11 throughout the course of the experiment. Reduction in mucositis scores was essentially equivalent between both topical groups. Interestingly, the effect of topically applied rhIL-11 was the same as the subcutaneously administered peptide from day 11 to the conclusion of the experiment.

Evaluation of the effect of rhIL-11 on moderate to severe mucositis demonstrated a similar trend. From day 6 to day 9, the percentage of control animals (group 1) with moderate to severe mucositis was markedly greater than that noted in animals treated with rhIL-11. In general, animals treated subcutaneously responded more favorably. For example, on day 8, 67% of control animals had mucositis scores equal to or greater than 5 compared to 13% of animals in group 2 and 31% of animals in group 4. The frequency of animals in the topically treated groups was 42% (group 3) and 39% (group 5). This trend appears to have shifted on days 10 to 11 where it appears that topically treated animals did better than those injected with rhIL-11. While this is true of surviving animals, evaluation of survival data is of importance in interpreting this apparent trend.

The above results demonstrate that topical administration of rhIL-11 is beneficial in vivo for the treatment of oral mucositis.

EXAMPLE 3

TREATMENT OF COLITIS (COLONIC ULCERS)

The effects of three different dosages of recombinant human interleukin-11 (rhIL-11), given subcutaneously (SC) either prior to or subsequent to intracolonic administration of trinitrobenzene sulfonic acid (TNB), were studied in Sprague-Dawley rats. The TNB or control were given in a 40% ethanol solution to 312 anesthetized adult male rats allotted to one of 26 groups (n=12). Control groups were: subcutaneous (SC); saline alone; intrarectal (IR); 40% ethanol alone; TNB alone; 40% ethanol alone, and SC, rhIL-11 at the highest dosage alone and groups combining TNB with rhIL-11 therapy, testing three dosages (100, 300, and 1,000 μg/kg), given either before or after induction of colitis with TNB. Body weight changes were monitored. Rats were euthanized at 3 days, 7 days, or 14 days after TNB administration. At necropsy, samples were collected to evaluate fecal occult blood, mucosal myeloperoxidase activity and mucosal gross indexes of ulceration. Histopathologic and ultrastructural analyses of the colonic mucosa were performed. The TNB alone elicited a prolonged, severe colitis in treated animals, and the ethanol control group showed a short-lasting, less severe colonic inflammatory response. Colonic ulcer indexes of rhIL-11 treated rats showed a consistent, dose-related reduction in the severity of the TNB-induced colitis, whether the interleukin was given before or after the TNB. This reduction was significant (P<0.05) after administration of the intermediate (300 μg/kg) and highest (1,000 μg/kg) dose levels of rhIL-11, in the groups given rhIL-11 for 7 days after TNB. Myeloperoxidase activity was increased during the TNB-induced colitis and was reduced by rhIL-11 administration (P<0.01). Fecal occult blood loss increased with colitis and paralleled its severity. rhIL-11 enhanced mucus production and decreased the severity of TNB-induced colitis.

EXAMPLE 4

TREATMENT OF MUCOSITIS

One of the dose-limiting toxicities of radiation therapy for head and neck cancer is the occurrence of oral mucositis. The effects of topical administration of IL-11 on this effect are examined in conjunction with at least one of several regimens employed for the treatment of advanced head and neck cancer. The specifics of the regimens vary, and may include external beam standard fractionated irradiation, hyperfractionated irradiation, or accelerated fractionated irradiation. Various chemotherapy agents may also be employed either sequentially or concurrently with radiotherapy. Chemotherapy agents frequently employed in this setting include 5-fluorouracil (5-FU), cisplatin, carboplatin, hydroxyurea, paclitaxel, and topotecan, either alone or in various combinations.

One regimen is outlined for the purpose of illustration. The regimen involves hyperfractionated external beam irradiation and concurrent chemotherapy with infusional 5-FU and cisplatin. This regimen has been employed for several years for patients with locally advanced squamous cell carcinoma of the head and neck. Patients receive 125 centi-Gray (cG) twice per week of external beam irradiation 5 days per week. The total planned dose is 7000 cG. During weeks 1 and 6 of radiotherapy, patients are treated with 5-FU and cisplatin. 5-FU is administered as a 5-day continuous infusion of 600 mg/m/day while cisplatin is administered as a bolus injection of 12 mg/m/day for 5 days. There is a 7-day scheduled treatment break after 4000 cG to allow mucositis to subside. The entire planned time for completion of the course of irradiation and concurrent chemotherapy is 7 weeks.

Patients are randomly assigned in a ratio of 2:1 to receive either topical IL-11 or placebo. Patients receiving IL-1 will receive either 50 μg/L or 150 μg/mL in 15 to 30 mL of Brioschi (sodium bicarbonate). A 5 mg vial of IL-11 or excipient alone [placebo] first will be resuspended with 1 mL water for injection (WFI). When 30 mL of Brioschi is used, 300 μL (for 50 ug/mL dose) or 950 μL (for the 150 ug/nL dose) containing either IL-11 or excipient alone will be removed from the vial and added to 30 mL Brioschi. This final preparation, containing either IL-11 or placebo excipient alone, is swished and swallowed twice daily for 6 to 8 weeks beginning the day before radiotherapy. All patients are assessed to determine the effects of the topical preparation of IL-11 on patients receiving chemotherapy and/or radiotherapy for head and neck cancer. Among the endpoints summarized are:

Incidence of oral mucositis of Grade 3 or higher, as measured by the modified National Cancer Institute Common Toxicity Criteria;

Duration of oral mucositis of Grade 3 or higher. Duration is measured as (1) the time from onset of Grade 3 or higher until resolution to less than Grade 3 and (2) the number of days of oral mucositis of Grade 3 or higher;

Total duration of oral mucositis of any grade;

Maximum severity of oral mucositis experienced during the study;

Incidence of hospitalization due to oral mucositis; and

Incidence of IV fluid resuscitation due to dehydration secondary to poor oral intake [secondary to mucositis].

Patients receiving IL-11 exhibit significant improvement in one or more of the above criteria.

EXAMPLE 5

TREATMENT OF PSORIASIS

The effects of IL-11 in modulating keratinocyte (the target cell type in a number of cutaneous inflammatory skin diseases, including psoriasis) growth and gene expression were assessed in vitro. When rhIL-11 (recombinant human IL-11) was added to a basal culture medium at a concentration of 100 ng/mL, it stimulated keratinocyte proliferation. RT-PCR analysis showed that keratinocytes grown in basal as well as enriched medium expressed IL-11 receptor a-chain mRNA (IL-11Rα). rhIL-11 was able to stimulate phosphorylation of STAT-3 in keratinocytes when grown in basal medium. To assess whether rhIL-11 could affect the levels of surface intercellular adhesion molecule-1 (ICAM-1) induced by IFN-γ and TNF-α, ketaninocytes were exposed to IFN-γ and TNF-α for one hour before adding rhIL-11. Addition of rhIL-11 resulted in a significant decrease in the amount of surface ICAM-1. These results show that IL-11 has direct effects on keratinocytes, thereby downregulating cutaneous immune responses.

While the present invention has been described in terms of specific methods and compositions, it is understood that variations and modifications will occur to those skilled in the art upon consideration of the present invention.

Numerous modifications and variations in the invention as described in the above illustrative examples are expected to occur to those skilled in the art and, consequently, only such limitations as appear in the appended claims should be placed thereon. Accordingly, it is intended in the appended claims to cover all such equivalent variations which come within the scope of the invention as claimed.

The disclosure of all of the publications cited herein are hereby incorporated by reference.

We claim:

1. A method of treating an inflammatory bowel disease in a patent comprising administering to the patient a topical formulation of a pharmaceutical composition containing a pharmaceutically effective amount of Interleukin-11 (IL-11).

2. The method of claim 1 wherein the inflammatory bowel disease is Crohn's disease.

3. The method of claim 1 wherein the inflammatory bowel disease is ulcerative colitis.

4. The method of claim 1 wherein the inflammatory bowel disease is indeterminate colitis.

5. The method of claim 1 wherein the inflammatory bowel disease is infectious colitis.

6. The method of claim 1 wherein the pharmaceutically effective amount of IL-11 is between about 1 and about 250 μg/kg body weight.

7. The method of claim 1 wherein the pharmaceutical composition is in the form of an oral solution, gel, suspension, pill, tablet, lozenge or capsule.

8. The method of claim 7 wherein the pharmaceutical composition comprises a oral solution of IL-11 in a suitable liquid carrier.

9. The method of claim 8 wherein the liquid carrier is selected from the group consisting of water, organic solvents, oils and fats.

10. The method of claim 9 wherein the liquid carrier is sodium bicarbonate.

11. The method of claim 10 wherein the liquid carrier is infant formula.

12. The method of claim 1 wherein the pharmaceutical composition additionally contains an immediate release carrier for release of IL-11 in the gastrointestinal tract of the patient.

13. The method of claim 12 wherein the immediate release carrier is selected from the group consisting of sugars, glycine, lactose, dextrin, starch, gelatin, cellulose, methyl cellulose, hydroxyprobylmethyl cellulose and sodium carboxymethyl cellulose.

14. The method of claim 1 wherein the pharmaceutical composition additionally contains a sustained release carrier for sustained release of IL-11 in the gastrointestinal tract of the patient.

15. The method of claim 1 wherein the pharmaceutical composition additionally comprises a proteinase inhibitor.

16. The method of claim 15 wherein the proteinase inhibitor is selected from the group consisting of aprotinin, α-macroglobulin, soybean trypsin inhibitor and ovomucoid.

17. The method of claim 16 wherein the proteinase inhibitor is aprotinin.

18. The method of claim 17 wherein the pharmaceutical composition form is a pill, tablet, lozenge or capsule and includes an enteric coating.

19. The method of claim 18 wherein the enteric coating is selected from the group consisting of a methacrylic acid-methacrylic acid ester-based copolymer, an anionic water-soluble polymer cellulose ether, cellulose acetate phthalate, polyvinyl acetate phthalate, and hydroxypropyl methylcellulose phthalate.

* * * * *